United States Patent [19]

Mulligan et al.

[11] Patent Number: 5,128,142
[45] Date of Patent: * Jul. 7, 1992

[54] SUSTAINED RELEASE DRUG DELIVERY SYSTEM

[75] Inventors: Seamus Mulligan, Athlone, Ireland; Randall T. Sparks, Gainesville, Ga.

[73] Assignee: Elan Corporation, plc, Athlone, Ireland

[ * ] Notice: The portion of the term of this patent subsequent to May 14, 2008 has been disclaimed.

[21] Appl. No.: 395,670

[22] Filed: Aug. 17, 1989

Related U.S. Application Data

[63] Continuation of Ser. No. 9,754, Feb. 2, 1987, abandoned.

[30] Foreign Application Priority Data

Feb. 3, 1986 [IE] Ireland .................................. 306/86

[51] Int. Cl.$^5$ ...................... A61K 9/20; A61K 37/20; A61K 9/22
[52] U.S. Cl. .................... 424/457; 424/461; 424/462; 424/469; 424/486; 424/488; 514/356; 514/964; 514/965
[58] Field of Search ............... 424/461, 462, 469, 486, 424/488, 80, 457; 514/356, 964, 965

[56] References Cited

U.S. PATENT DOCUMENTS

| | | | |
|---|---|---|---|
| 3,951,851 | 4/1976 | Kitajima et al. | 424/469 |
| 4,369,172 | 1/1983 | Schor et al. | 424/19 |
| 4,389,393 | 6/1983 | Schor et al. | 424/19 |
| 4,412,986 | 11/1983 | Kawata et al. | 424/80 |
| 4,539,199 | 9/1985 | Orban et al. | 424/462 |
| 4,540,566 | 9/1985 | Davis et al. | 514/964 |
| 4,562,069 | 12/1985 | Hegasy et al. | 514/356 |
| 4,568,536 | 2/1986 | Kronenthal et al. | 514/964 |
| 4,587,118 | 5/1986 | Hsiano | 514/964 |
| 4,666,704 | 5/1987 | Shalati et al. | 514/965 |
| 4,695,467 | 9/1987 | Uemura et al. | 424/464 |
| 4,753,801 | 6/1988 | Oren et al. | 424/465 |
| 4,784,858 | 11/1988 | Uentouras | 424/469 |
| 4,973,469 | 11/1990 | Mulligan et al. | 424/461 |

FOREIGN PATENT DOCUMENTS

| | | |
|---|---|---|
| 1184118 | 3/1985 | Canada . |
| 92060 | 10/1983 | European Pat. Off. . |
| 78430 | 9/1984 | European Pat. Off. . |
| 123668 | 10/1984 | European Pat. Off. . |
| 0135022 | 3/1985 | European Pat. Off. . |
| 167909 | 6/1985 | European Pat. Off. . |
| 2549740 | 5/1977 | Fed. Rep. of Germany . |
| 3326167 | 2/1985 | Fed. Rep. of Germany . |
| 3400106 | 7/1985 | Fed. Rep. of Germany . |
| 61-161215 | 7/1986 | Japan . |
| 1504553 | 3/1978 | United Kingdom . |

OTHER PUBLICATIONS

Remington's Pharmaceutical Sciences, (17th Edition, 1985), pp. 1644–1647.
Chemical Abstracts, vol. 97, No. 10, Sep. 6, 1982, abstract 97:78923a.
Chemical Abstracts, vol. 95, No. 24, Dec. 14, 1981, abstract 95:209672(b).

Primary Examiner—Ronald W. Griffin
Attorney, Agent, or Firm—Church, Marla J.

[57] ABSTRACT

A controlled release formulation comprising an adsorbate of a mixture of a pharmaceutically useful active ingredient and an inactive substance adsorbed on a cross-linked polymer. The inactive substance is selected to modify the dissolution of the active ingredient from the cross-linked polymer in vivo.

12 Claims, No Drawings

SUSTAINED RELEASE DRUG DELIVERY SYSTEM

This is a continuation of application Ser. No. 009,754, filed on Feb. 2, 1987, now abandoned.

BACKGROUND OF THE INVENTION

This invention relates to a method for the manufacture of adsorbates for use in drug delivery systems and to the adsorbates and drug formulations thereby obtained.

It is frequently desirable to delay the release of an active substance from a pharmaceutical formulation in vivo. For example, it may be desirable to delay release of the active substance within the body so that the active substance is released at a particular target site. Various coated tablets are available which are resistant to gastric juices but which are readily soluble in the higher pH environment of the small intestine. Various controlled absorption pharmaceutical formulations are also available which have a particular dissolution pattern, resulting in a controlled absorption of the active substance and, therefore, more effective medication.

The use of many active substances in therapy is complicated by solubility problems. In the case of some insoluble drugs like nifedipine co-precipitates thereof with certain polymers are known, said co-precipitates having been formed into tablets by conventional tabletting procedures. Such co-precipitates however normally require a polymer to active drug ratio exceeding 3:1 in order to be effective in producing products characterised by high bioavailability with prompt peak blood levels.

Pharmaceutical formulations based on an adsorbate of a drug within a cross-linked polymer, such as crosspovidone, are also known. Furthermore, solid, rapidly absorbable medicament formulations comprising a dihydropyridine, polyvinylpyrrolidone with an average molecular weight of 15,000 to 50,000 and cross-linked insoluble polyvinylpyrrolidone are known from EP-A-0 167 909.

It is an object of the present invention to provide an improved drug delivery system wherein the bioavailability of an otherwise poorly bioavailable active substance is enhanced and effective controlled and sustained, release formulations thereof can be produced.

SUMMARY OF THE INVENTION

Accordingly, the invention provides a controlled release formulation comprising an adsorbate of a mixture of 1 part by weight of a pharmaceutically useful active ingredient and from 0.1 to 10 parts by weight of an inactive substance adsorbed on a cross-linked polymer in a ratio of 1 part by weight of said mixture to 0.5-20 parts by weight of cross-linked polymer, said inactive substance being selected to modify the dissolution of the active drug from the cross-linked polymer in vivo, with the proviso that the active ingredient is not a dihydropyridine when the inactive substance is polyvinylpyrrolidone with an average molecular weight in the range 15,000 to 50,000 and the cross-linked polymer is cross-linked polyvinylpyrrolidone.

The invention also provides a sustained release drug delivery system comprising a mixture of 1 part by weight of a pharmaceutically useful active ingredient and from 0.1-10 parts by weight of inactive substance, wherein 1 part by weight of said mixture is adsorbed on 0.5-20 parts by weight of a cross-linked polymer, wherein said inactive substance is selected to modify the dissolution of the active ingredient from the cross-linked polymer in vivo and said active ingredient is in substantially amorphous form, the resultant adsorbate being granulated and blended with a polymer or mixture of polymers to yield a long-acting controlled release matrix system.

DETAILED DESCRIPTION OF THE INVENTION

The existence of the drug (active ingredient) in the pore spaces of the cross-linked polymer can be confirmed by x-ray diffraction studies. In the case of certain water-insoluble drugs, the formation of the adsorbate results in an amorphous state which can be verified by x-ray diffraction and, in addition, differential scanning calorimetery.

The inactive substance is preferably present in the adsorbate in an amount of 0.5-3 parts by weight relative to 1 part by weight of the active ingredient. Furthermore, the formulation preferably contains 1 part by weight of said mixture relative to 1-10 parts by weight of cross-linked polymer.

The invention also provides a process for preparing a controlled release formulation as defined above, which comprises dissolving the active ingredient and the inactive substance in a common solvent, mixing the solution thereby obtained with a given quantity of the cross-linked polymer so as to permit adsorption of said active ingredient and said inactive substance to said cross-linked polymer and removing the solvent.

The solvent used is any pharmaceutically suitable co-solvent for the active drug and the inactive substance.

The solvent is suitably selected from water, alcohols, ketones, halogenated aliphatic compounds, halogenated aromatic hydrocarbon compounds, aromatic hydrocarbon compounds and cyclic ethers or a mixture thereof.

Especially preferred solvents include water, hexane, heptane, methanol, ethanol, isopropyl alcohol, acetone, methylethyl ketone, methylisobutyl ketone, methylene chloride, chloroform, carbon tetrachloride, toluene, xylene and tetrahydrofuran.

Those of ordinary skill in the art will appreciate that other solvents that are effective for dissolving the active ingredient and the inactive substance may also be used.

The inactive substance is chosen to modify the dissolution of the active drug from the cross-linked polymer such that a water soluble inactive substance will serve to enhance the rate of active drug leaching from the cross-linked polymer. Conversely, a water insoluble material would serve to impede the rate of active ingredient leaching from the cross-linked polymer as will be appreciated by one skilled in the art.

The inactive substance is also chosen to modify the crystalline properties of the active ingredient both in the controlled release formulation as prepared and in vivo after administration of the formulation.

An especially preferred cross-linked polymer is crosspovidone (Polplasdone XL (GAF), Kollidon CL (BASF) Polplasdone XL and Kollidon CL are Trade Marks). Others include cross-linked carboxymethylcellulose and cross-linked methylcellulose.

Any drug, subject to the above proviso, is suitable for use as active ingredient in the formulation according to the present invention. However, preferred drugs include ibuprofen, acylovir, 5-amino-salicyclic acid, dextromethorphan, propranolol, theophylline, methyldopa, pseudoephedrine, cimetidine, cephalexin, cephaclor, cephradine, naproxen, piroxicam, diclofenac, indomethacin, amoxycillin, pivampicillin, bacampicillin, dicloxacillin, erythromycin, lincomycin, co-dergocrine mesylate, doxycycline, dipyridamole, frusemide, triamterene, sulindac, nifedipine, nicardipine, 4-(2, 1, 3-bensoxadiasol-4-yl)-2, 6-dimethyl-1, 4-dihydro-3-isopropyloxycarbonyl-pyridine-5-carboxylic acid methyl ester, atenolol, lorazempam, glibenclamide, salbutamol, spironolactone, chlorpheniramine maleate, carboxamine maleate, potassium chloride and metoprolol tartrate.

Especially preferred active ingredients include chlorpheniramine, diclofenac, theophylline, felodipine, nifedipine, nicardipine, nitrendipine, 4-(2, 1, 3-benzoxadiazol-4-yl)-2,6-dimethyl-1,4-dihydro-3-isopropyloxycarbonyl-pyridine-5-carboxylic acid methyl ester, co-dergocrine mesylate, oxendolone, azidothymidine (AZT) and spironolactone.

The choice of inactive substance for use in controlling the dissolution of the adsorbed active drug according to the present invention is determined by the particular pharmacological properties desired. As will be appreciated by one skilled in the art, for example, a water insoluble inactive substance may be used to delay the release of a highly water soluble drug. Similar results could be obtained with a polymer of low porosity or a polymer which is only slightly permeable to water when such is used as the inactive substance.

Examples of inactive substances include inert polymers such as, for example, polyvinyl alcohol, polyvinylpyrrolidone, hydroxyethylcellulose, hydroxypropylcellulose, hydroxypropylmethylcellulose, sodium carboxymethylcellulose, alkyl-celluloses such as methyl- and ethylcellulose, shellac, polymers sold under the trademark Eudragit, polyethylene glycol, sodium alginate, galactomannone or carboxypolymethylene or mixtures thereof.

Eudragit polymers are polymeric lacquer substances based on acrylates and/or methacrylates.

Especially suitable Eudragits for use as inactive substances in the system according to the invention include co-polymers of acrylic and methacrylic acid esters of varying permeability to the active ingredient and aqueous media.

Other suitable inactive substances for use in the system according to the invention include sugars and many organic acids, such as adipic acid, ascorbic acid, citric acid, fumaric acid, maleic acid, succinic acid or tartaric acid.

The choice of inactive substance is generally made by reference to the solubility of the active substance and will usually have its own solubility inversely proportional to that of the active drug. Therefore, water insoluble, polymeric materials have use in conjunction with highly water-soluble active drugs as will be appreciated by one skilled in the art.

The invention also provides a sustained release drug delivery system comprising a controlled release formulation as defined above, suitably granulated and blended with a polymer or mixture of polymers which gels in the presence of water, and optionally other ingredients. The blend thereby obtained can be tabletted or encapsulated according to conventional methods, thereby yielding a long acting controlled release matrix system which also exhibits improved drug absorption. Suitable polymers for blending with the controlled release formulation for subsequent tabletting or encapsulation are any one of the inert polymers cited above, which include both water soluble and water insoluble polymers. An especially suitable group of polymers is the polymers sold under the Trade Mark Methocel. If one wishes to delay release of the active ingredient in vivo in capsule or tablet form a combination of a water soluble and a water insoluble polymer or a mixture of such polymers will be used, with the ratio of the water soluble to water insoluble polymer being varied to give the desired rate of release. Similarly, in the case of polymers/copolymers of varying permeability the permeabililty characteristic of the polymers/copolymers will be chosen to give the desired rate of release.

The adsorbates according to the present invention result in improved controlled drug delivery relative to known active drug adsorbates in cross-linked polymers, since the adsorbates according to the present invention yield a matrix system exhibiting both delayed or sustained release of active drug and improved absorption of said active drug in vivo when granulated and blended with pharmaceutically acceptable polymers.

The invention will be further illustrated with reference to the following Examples.

EXAMPLE 1

Polyvinylpyrrolidone K-30 (Trade Mark) (2 kg) was dissolved in isopropylalcohol (10 kg). Nifedipine (1 kg) was then added to this solution and allowed to dissolve. The solution thereby obtained was then adsorbed onto cross-linked carboxymethylcellulose (4 kg) and the solvent evaporated. The resulting powder was then passed through an oscillating granulator to obtain a finer particle size. X-ray diffraction and differential scanning calorimetry studies were performed on the powder and demonstrated that the nifedipine was in an amorphous form. The powder (30%) was then tabletted with the following ingredients:

| | |
|---|---|
| Methocel K100LV (Trade Mark) | 8.0% |
| Avicel pH101 (Trade Mark) | 61.5% |
| Magnesium stearate | 0.5% | to obtain a tablet containing 20 mg of active ingredient. An x-ray diffraction pattern of the tablet was obtained which demonstrated the amorphous nature of the nifedipine had been retained.

In the above Example, the ratio of nifedipine, polyvinylpyrrolidone and cross-linked carboxymethylcellulose may be altered within the limits which retain the amorphous nature of the drug. This also applies in the case of the subsequent Examples.

Furthermore, the Methocel used may be Methocel K4M, K15M, K100M, or E, J, F grades depending on the release characteristics desired.

The gel forming polymer may be used in an amount of 3-50% with proportional changes in the percentage of adsorbate used. This also applies in the case of the subsequent Examples.

EXAMPLE 2

Polyvinylpyrrolidone K-30 (Trade Mark) (2 kg) was dissolved in isopropyl alcohol (10 kg). Nicardipine (1 kg) was then added to this solution and allowed to dissolve. The solution thereby obtained was then adsorbed onto a cross-linked carboxymethylcellulose (Croscarmellulose—Trade Mark) (4 kg) and the solvent evaporated. The resulting powder was passed through an oscillating granulator to obtain a finer particle size. The powder (60%) was then tabletted with the following ingredients:

| Methocel K100M (Trade Mark) | 8.0% |
| Avicel pH101 (Trade Mark) | 31.5% |
| Magnesium stearate | 0.5% | to obtain a tablet containing 60 mg of active ingredient.

EXAMPLE 3

The procedure of Example 1 was repeated except that the nifedipine was replaced by an equal amount (1 kg) of (4-(2,1,3-benzoxadiazol-4-yl)-2, 6-dimethyl-1, 4-dihydro-3-isopropyloxycarbonyl-pyridine-5-carboxylic acid methyl ester to obtain tablets containing 10 mg mg of active ingredient.

EXAMPLE 4

Spironolactone (1 kg) and polyvinylpyrrolidone K-30 (2 kg) were dissolved in a common solvent ethanol (10 kg).

Cross-povidone (4 kg) was added to the solution of spironolactone and polyvinylpyrrolidone so as to permit adsorption of the spironolactone and polyvinylpyrrolidone to the cross-povidone. The solvent was then removed by heating. The ability of the spironolactone to be dissolved out of the cross-povidone is enhanced by the ready solubility of the polyvinylpyrrolidone in water. A given quantity (50%) of the adsorbate was granulated and blended with hydroxypropylmethylcellulose (50%). The blend thereby obtained was filled into soft gelatine capsules so as to obtain capsules containing (50 mg) of spironolactone.

EXAMPLE 5

Anhydrous theophylline (0.5 kg) and citric acid (1 kg) were dissolved in isopropyl alcohol (10 kg) and adsorbed on cross-povidone (2 kg) in the manner described in Example 1. An adsorbate between anhydrous theophylline and citric acid was thereby obtained. A given quantity (50%) of the adsorbate was granulated and blended with Eudragit RL (50%). The blend was then filled into hard gelatine capsules (422 mg) so as to obtain capsules containing 300 mg of anhydrous theophylline. The presence of the citric acid was found to enhance the solubility of the anhydrous theophylline at pH values in excess of 7 and was suitable for use in a long acting or sustained release drug formulation.

EXAMPLE 6

Chlorpheniramine maleate (0.5%) and ethylcellulose (1 kg) which is insoluble in water and thereby inactive in an aqueous environment were dissolved in isopropyl alcohol (10 kg) and adsorbed onto cross-povidone (2 kg) in the manner described in Example 1. The powder (30%) was then tabletted with the following ingredients:

| Methocel K15M (Trade Mark) | 8.0% |
| Avicel pH101 (Trade Mark) | 61.5% |
| Magnesium stearate | 0.5% | to obtain a tablet containing 10 mg of chlorpheniramine maleate.

EXAMPLE 7

Polyvinylpyrrolidone (K-30) (0.75 kg) was dissolved in methylene chloride (12 kg) nifedipine (1 kg) was then added to this solution and allowed to dissolve. The solution thereby obtained was then adsorbed onto cross-linked carboxymethylcellulose (3 kg) and the solvent evaporated. The resulting powder was then passed through an oscillating granulator to obtain a fine particle size. X-ray diffraction and differential scanning calorimetry studies showed that the drug was in amorphous form in this adsorbate. The powder (30%) was the tabletted with the following ingredients:

| Methocel K100LV (Trade Mark) | 10% |
| Avicel pH101 (Trade Mark) | 59.5% |
| Magnesium stearate | 0.5% | to obtain a tablet containing 20 mg active ingredient.

Similar x-ray diffraction and differential scanning calorimetry studies showed this product to be amorphous.

EXAMPLE 8

The procedure employed was similar to that in Example 7 except that the amount of polyvinylpyrrolidone (K-30) used was 0.5 kg and also included was polyethylene glycol 6000 (1 kg).

EXAMPLE 9

The procedure employed was similar to that in Example 8 except that the polyethylene glycol was replaced by methylcellulose (0.75 kg).

EXAMPLE 10

The procedure employed was similar to that in Example 7 except that methylcellulose (0.75 kg) was used instead of polyvinylpyrrolidone 0.75 kg.

EXAMPLE 11

The procedure employed was similar to that in Example 8 except that polyvinylpyrrolidone (0.5 kg) was replaced by methylcellulose (0.5 kg).

EXAMPLE 12

The procedure used was similar to that employed in Example 7 except the polyvinylpyrrolidone (0.75 kg) was replaced by polyethylene glycol 6000 (1.5 kg).

EXAMPLE 13

Polyvinylpyrrolidone K-25 (Trade Mark) (0.50 kg) was dissolved in isopropyl alcohol (10 kg). Diclofenac (1 kg) was added to this solution and allowed to dissolve. The solution thereby obtained was then adsorbed onto cross-linked polyvinylpyrrolidone (2.5 kg) and the solvent evaporated. The resulting powder (60%) was treated as in Example 1 and tabletted with the following ingredients:

| Methocel K100LV (Trade Mark) | 16.5% |
| Avicel pH101 (Trade Mark) | 23.0% |
| Calcium stearate | 0.5% | to obtain a tablet containing 100 mg active ingredient.

EXAMPLE 14

Methocel A4M (Trade Mark) (0.15 kg) was dissolved in dichloromethane (10 kg). Oxendolone (1 kg) was added to the solution and dissolved. The resulting solution was adsorbed onto cross-povidone (4 kg) and treated as per Example 1.

The resulting powder (80%) was tabletted with the following ingredients:

| Methocel K100LV (Trade Mark) | 1.5% |
|---|---|
| Avicel pH 10% (Trade Mark) | 13.0% |
| Magnesium stearate | 0.5% | to obtain a tablet containing 100 mg active ingredient.

EXAMPLE 15

Example 1 was repeated except the nifedipine formulation (50%) was tabletted with the following ingredients.

| Sodium alginate | 15.0% |
|---|---|
| Pregelatinized starch N.F. | 33.5% |
| Talc | 1.5% |

EXAMPLE 16

Example 2 was repeated except the nicardipine formulation (50%) was tabletted with the following ingredients:

| Lactose U.S.P. | 10.0% |
|---|---|
| Eudragit R.S. | 10.0% |
| Eudragit R.L. | 29.25% |
| Calcium stearate | 0.75% |

EXAMPLE 17

Example 6 was repeated except the chlorpheniramine maleate formulation (40%) was tabletted with the following ingredients.

| Dibasic calcium phosphate dihydrate N.F. | 15.0% |
|---|---|
| Ethylcellulose 100 cps | 15.0% |
| Polyethyleneglycol 6000 | 5.0% |
| Hydroxyethylcellulose | 29.0% |
| Calcium stearate | 1.0% |

What we claim is:

1. A sustained release drug delivery system comprising a mixture of 1 part by weight of a pharmaceutically useful active ingredient and from 0.1–10 parts by weight of inactive substance, wherein 1 part by weight of said mixture is adsorbed on 0.5–20 parts by weight of a cross-linked polymer, wherein said inactive substance is selected to modify the dissolution of the active ingredient from the cross-linked polymer in vivo and said active ingredient is in substantially amorphous form, the resultant adsorbate being granulated and blended with a polymer or mixture of polymers to yield a long-acting controlled release matrix system.

2. A sustained release drug delivery system according to claim 1, wherein the polymer or mixture of polymers gels in the presence of water.

3. A sustained release drug delivery system according to claim 2, wherein the polymer which gels in the presence of water is selected from the group consisting of polyvinyl alcohol, polyvinylpyrrolidone, hydroxyethylcellulose, hydroxypropylcellulose, hydroxypropylmethylcellulose, sodium carboxymethylcellulose, alkylcelluloses, copolymers of acrylic and methacrylic acid esters, shellac, polyethylene glycol, sodium alginate, galactomannone or carboxypolymethylene or mixtures thereof.

4. A sustained release drug delivery system according to claim 3, wherein the polymer which gels in the presence of water is selected from the group consisting of methylcellulose, ethylcellulose, hydroxypropylcellulose, hydroxypropylmethylcellulose, or a copolymer of acrylic and methacrylic acid esters or a mixture thereof.

5. A sustained release drug delivery system according to claim 3, wherein said gel forming polymer is present in an effective amount between 3 to 50% by weight of the system.

6. A sustained release drug delivery system according to claim 1, wherein the active ingredient is a dihydropyridine, the inactive substance is a polyvinylpyrrolidone, polyethylene glycol or methylcellulose or mixtures thereof, and the cross-linked polymer is a cross-linked polyvinylpyrrolidone, carboxymethylcellulose or methylcellulose.

7. A sustained release drug delivery system according to claim 6, wherein the inactive substance is present in an amount of 0.5–3 parts by weight relative to 1 part by weight of the active ingredient.

8. A sustained release drug delivery system according to claim 6, which contains 1 part by weight of said mixture relative to 1–10 parts by weight of cross-linked polymer.

9. A sustained release drug delivery system according to claim 6, wherein the kihydropyridine is selected from the group consisting of felodipine, nicardipine, nifedipine, nitrendipine, nimodipine, nisoldipine and 4-(2,1,3-bensoxadiasol-4-yl)-2, 6-dimethyl-1, 4-dihydro-3-isopropyloxycarbonyl-pyridine-5-carboxylic acid methyl ester.

10. A process for preparing a sustained release drug delivery system according to claim 1, which comprises dissolving the active ingredient and the inactive substance in a common solvent, mixing the solution thereby obtained with a given quantity of the cross-linked polymer so as to permit adsorption of said active ingredient and said inactive substance to said cross-linked polymer to form the adsorbate, removing the solvent, granulating and blending said adsorbate with the polymer or mixture of polymers to yield the long-acting controlled release matrix system.

11. A process according to claim 10, wherein the solvent used is any pharmaceutically suitable co-solvent for the active ingredient and the inactive substance.

12. A process according to claim 11, wherein the solvent is selected from the group consisting of water, alcohols, ketones, halogenated aliphatic compounds, halogenated aromatic hydrocarbon compounds, aromatic hydrocarbon compounds or cyclic ethers or a mixture thereof.

* * * * *